United States Patent
Guray

(10) Patent No.: US 6,726,473 B1
(45) Date of Patent: Apr. 27, 2004

(54) TEMPORARY AND INSTANT BITE RAISER IN THE FIXED ORTHODONTIC TREATMENTS

(76) Inventor: Enis Yasar Guray, Cinnah Cad., No. 37/3, 06880 Cankaya-Ankara (TR)

(*) Notice: Subject to any disclaimer, the term of this patent is extended or adjusted under 35 U.S.C. 154(b) by 0 days.

(21) Appl. No.: 10/089,046
(22) PCT Filed: Sep. 23, 1999
(86) PCT No.: PCT/TR99/00042
§ 371 (c)(1), (2), (4) Date: Sep. 6, 2002
(87) PCT Pub. No.: WO01/21090
PCT Pub. Date: Mar. 29, 2001
(51) Int. Cl.[7] ............................................ A61C 3/00
(52) U.S. Cl. ........................................ 433/6; 433/19
(58) Field of Search ......................... 433/17, 19, 6

(56) References Cited

U.S. PATENT DOCUMENTS

| | | | |
|---|---|---|---|
| 4,439,149 A | * 3/1984 | Devincenzo | 433/6 |
| 4,671,766 A | * 6/1987 | Norton | 433/6 |
| 5,203,324 A | 4/1993 | Kinkade | |
| 5,848,891 A | * 12/1998 | Eckhart et al. | 433/19 |
| 5,879,155 A | * 3/1999 | Kittelson | 433/6 |
| 5,957,686 A | * 9/1999 | Anthony | 433/19 |
| 6,012,919 A | * 1/2000 | Cross, III et al. | 433/6 |
| 6,099,304 A | * 8/2000 | Carter | 433/19 |

* cited by examiner

Primary Examiner—Cary E. O'Connor
(74) Attorney, Agent, or Firm—Nixon & Vanderhye

(57) ABSTRACT

The dental appliance includes a bite raiser body having vestibular and palatal sides. The vestibular side includes proximal wings for connecting the body to a molar tube. The body includes arms diverging toward the palatal side and terminating in an interconnecting base. A T-shaped spur projects outwardly from the base. The arms include a pair of occlusal stops and the base has an occlusal stop, all stops projecting within the arms and base. By connecting the insertion wings to the molar tube and connecting the spur to the tooth, the occlusal stops overlie the occlusal surface, raising the bite.

7 Claims, 1 Drawing Sheet

TEMPORARY AND INSTANT BITE RAISER IN THE FIXED ORTHODONTIC TREATMENTS

Orthodontic treatments are performed by using removable and fixed appliances. Fixed appliances methods are developing continually.

The prevention of the occlusal contacts may be occasionally necessary during fixed orthodontic treatments. Treatment of some cases such as deep-bite, cross-bite and scissors-bite with fixed appliances, it is usually necessary to open the bite temporarily in order to prevent bracket shearing and to allow for easy tooth movement.

In the treatment of deep bite cases, bonding of the lower incisors requires a certain time. Since, on such cases the bite must be opened sufficiently before bonding, of the lower incisors. Otherwise, the upper incisors may cause the shearing of those brackets.

In the treatments of the "buccal non-occlusion" and "telescopic bites", the bite must also be raised to allow for easy tooth movement.

Likewise, in the treatment of the "anterior and posterior cross-bites"; temporarily opening the bite will ensure easy tooth movement and easy expansion in a short time.

Out of the above mentioned reasons, raising the bite, may be necessary in many cases.

Temporary and instant raising of the bite, during fixed orthodontic treatments are commonly obtained by using removable occlusal plates. However, the application of these plates, beside of their difficulty of usage, requires complete patient co-operation.

Bonding of restorative materials on the occlusal surfaces of the posterior teeth can be performed, alternatively. Application of these materials is an appropriate method for bite opening however the adhesive force of these materials is nor sufficient to resist to the occlusal forces due to the absence of cavity preparation. Also, this method could not ensure the hygiene since, the rest of these materials could not be cleaned sufficiently after their usage.

Review of the literature revealed that this subject is quiet ignored. Fine, in deep-bite cases, has bonded "Begg" brackets to the maxillary central incisors to prevent the shearing of the lower incisor brackets. Furthermore, the shearing of the lower brackets were tried to be prevented by using lingual brackets which are as fragile as the lowers. More over, this is not an invention, nor a different wire bending. This is a different use of the existing treatment accessories.

J. Donald Kinkade has developed an anatomical mouthpiece which relates to mouthpieces which are used in underwater breathing devices such as snorkels and regulators and also to mouthpieces which are used in inhalators and gastric tubes for medical treatments (Document U.S Pat. No. 5,203,324). This device is used to facilitate breathing for scuiba divers and patients who are attached to life supporting medical machines. Although this device has an occlusal part, it has not any relation with "bite raising in orthodontics" nor "bite opening".

To solve the limitation of instant and temporary bite raising during fixed orthodontic treatments, I developed a special wire bending and I published it's usage as a case report in the Journal of Turkish Orthodontic Society, in 1995. Same year, I presented it in the name of "Semi-fixed Temporary Bite-raiser" in the 71$^{th}$ Congress of European Orthodontic Society, in Bergen-Norway. This article is also published in the April 1999 issue of the Journal of Clinical Orthodontics. Since it's first publication, with my clinical experiences, I developed the original model and reached to it's final form, which became now available to the serial fabrication. In other words, it resembles to it's original by it's function, but it's form and usage facilities are totally developed. Due to these properties, it became also a commercial article.

The aim of this invention, is to instantly and temporarily raise the bite, as described above. However, the most important is that the bite-raiser does not necessitate patient co-operation since, it is tightened to the molar tube by its proximal wings and this peculiarity ensures success of the treatment, in a short time. Furthermore, it is also valuable for its optimal hygienic conditions. It has no pathological effects on the molars due to its temporary usage. Molar intrusion may be observed in a long time application and this reversible tooth movement can be compensated with arch bending.

This instant and temporary bite raiser can be preferred and recommended on

Figure 1:
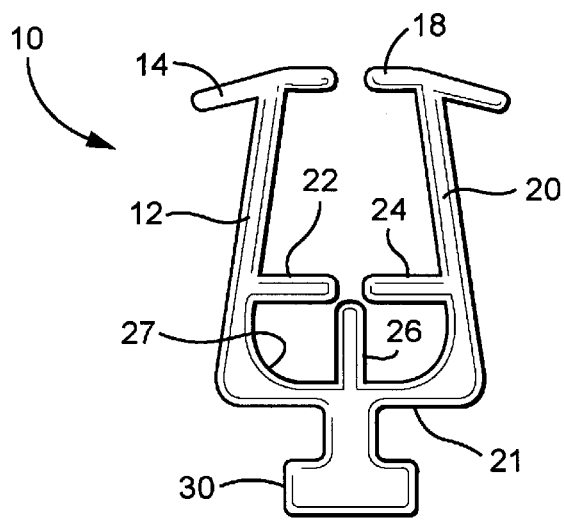
FIG. 1 is a plan view of a bite raiser in accordance with a preferred embodiment of the present invention.
Figure 2:
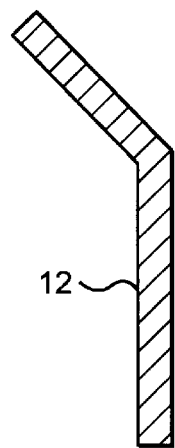
FIG. 2 is a side elevational view of the bite raiser of FIG. 1 angled to overlie the occlusal surfaces of a tooth.
Figure 3:
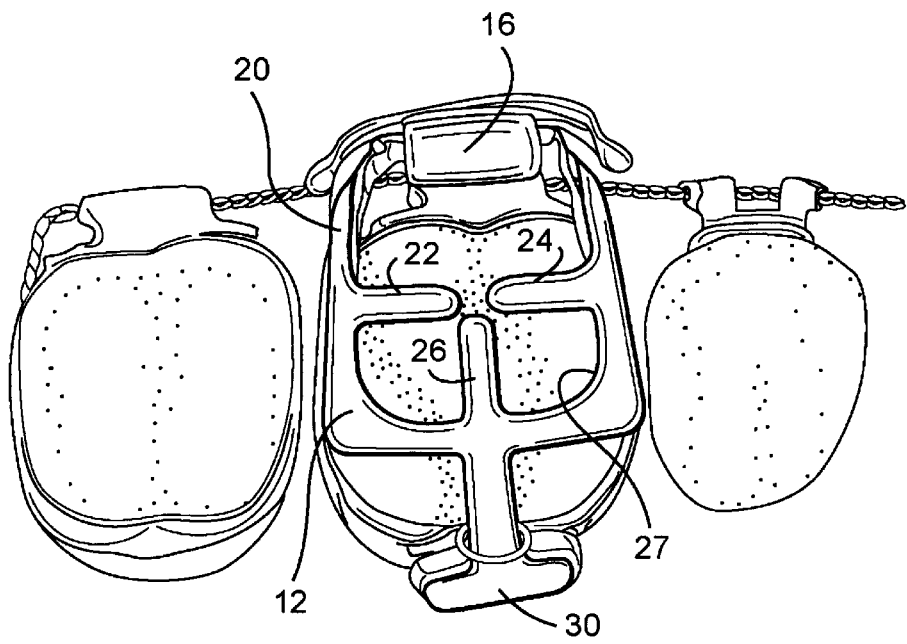
FIG. 3 is a plan view of the bite raiser hereof mounted on the tooth.

The dental appliance hereof, i.e., the bite raiser, generally designated 10, preferably includes a bite raiser body 12 constructed from 0.8–1.0 mm. Cr—Ni, titanium, stainless steel or similar metals. The vestibular side of body 12 includes a pair of insertion wings 14 serving to insert the bite raiser into the molar tube 16 (FIG. 3) and a pair of proximal wings 18, extended from the insertion wings 14. Wings 18 serve to attach the bite raiser 10 to the molar tube by an elastic ring or a ligature wire. Body 12 includes first and second arms 20 extending between vestibular and palatal sides of the body 12 for in part overlying the occlusal surface of the tooth with an angle according to the anatomical form of the molar tooth (FIG. 3). The arms terminate at respective opposite ends of a base 21 on the palatial side of body 12. For overlying the occlusal surface, three occlusal stops 22, 24 and 26 are provided. Stops 22 and 24 extend inwardly from the arms 20 toward one another. Stop 26 extends from base 21 toward stops 22 and 24. Stops 22, 24 and 26 can be bent to the occlusal pits of the molar tooth to increase the stability and height of the bite raiser. The body 12 is wider on the palatal side and narrow on the vestibular side with arms 20 inclined toward one another in a direction toward the vestibular side. This shape enables reinforced palatal angles between the base 21 and arms 20, on the palatal cusps of the molar tooth. The reinforcement is made by widening the metal surface on the palatal angles, i.e., by having large interior radii 27 between the arms 20 and base 21. On the palatal side, there is a "T" shaped palatal spur 30 (or T-hook), serving to attach the raiser to the palatal part of the molar band (FIG. 3). This T-hook could also be bent to the opposite side, in the condition of the insufficiency of raising the bite, i.e., to extend the raise of the bite.

FIG. 3 illustrates the dental appliance body 12 overlying the occlusal surface of a tooth with the insertion wings 14 in the molar tube and the proximal wings 18 facilitating attachment of the bite raiser to the molar tube by an elastic ring or ligature wire.

I claim:

1. A dental appliance for temporarily raising an individual's bite comprising:
   a bite raiser body having vestibular and palatal sides connected to one another by a pair of spaced arms inclined toward one another in a direction toward the vestibular side;

said vestibular side having a pair of wings projecting laterally for insertion into a molar tube to secure the appliance on a vestibular side of a tooth;

said arms on the palatal side terminating in a base interconnecting said arms;

first and second stops extending from said arms in a direction generally toward one another intermediate said wings and said base and a third stop extending from said base and between said arms, said stops being located to overlie occlusal surfaces of the tooth;

said palatal side including a palatal spur projecting from said base in a direction away from said stops for securement to the tooth.

2. A dental appliance according to claim 1 wherein said spur is generally T-shaped.

3. A dental appliance according to claim 1 including a pair of proximal wings forming continuations of the insertion wings to facilitate securement of the body to the molar tube.

4. A dental appliance according to claim 1 wherein said stops are deformable to extend into occlusal pits of the molar tooth.

5. A dental appliance according to claim 1 wherein said arms project from opposite ends of said base and have regions between each arm and the base for reinforcing the juncture of the arms and the base adjacent opposite ends of said base.

6. A dental appliance according to claim 5 wherein said regions include large radii along inside surfaces of the arms and the base at each juncture therebetween.

7. A dental appliance according to claim 1 wherein said third stop extends from said base and terminates short of said first and second stops.

* * * * *